United States Patent
Kaufmann et al.

(10) Patent No.: US 10,245,084 B2
(45) Date of Patent: *Apr. 2, 2019

(54) RESILIANT SPINAL PLATE SYSTEM

(71) Applicant: Genesys Spine, Austin, TX (US)

(72) Inventors: Joshua Kaufmann, Austin, TX (US); Scott Bryant, Austin, TX (US); Greg Calbert, Austin, TX (US); Brian Bergeron, Austin, TX (US); Landon Gilkey, Austin, TX (US); John Stokes, Austin, TX (US); Matthew Geck, Austin, TX (US)

(73) Assignee: Genesys Spine, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/917,117

(22) Filed: Mar. 9, 2018

(65) Prior Publication Data

US 2018/0193072 A1 Jul. 12, 2018

Related U.S. Application Data

(63) Continuation of application No. 14/724,323, filed on May 28, 2015, now Pat. No. 9,913,672.

(60) Provisional application No. 62/003,984, filed on May 28, 2014.

(51) Int. Cl.
*A61B 17/80* (2006.01)
*A61B 17/70* (2006.01)

(52) U.S. Cl.
CPC ...... *A61B 17/8052* (2013.01); *A61B 17/7059* (2013.01); *A61B 17/8047* (2013.01)

(58) Field of Classification Search
CPC . A61B 17/7059; A61B 17/80; A61B 17/8004; A61B 17/8033; A61B 17/8038; A61B 17/8042; A61B 17/8047; A61B 17/8052; A61B 17/8057
See application file for complete search history.

(56) References Cited

U.S. PATENT DOCUMENTS

| | | |
|---|---|---|
| 5,549,612 A | 8/1996 | Yapp |
| 6,152,927 A | 11/2000 | Farris |
| 6,258,089 B1 | 7/2001 | Campbell |
| 6,361,537 B1 | 3/2002 | Anderson |
| 7,182,782 B2 | 2/2007 | Kirschman |
| 7,641,701 B2 | 1/2010 | Kirschman |
| 7,655,028 B2 | 2/2010 | Kirschman |
| 7,740,649 B2 | 6/2010 | Mosca |
| 8,216,285 B2 | 7/2012 | Markworth |
| 8,287,550 B2 | 10/2012 | Campbell |
| 8,454,666 B2 | 6/2013 | Tornier |
| 8,784,459 B2 | 7/2014 | Kaufman |

(Continued)

FOREIGN PATENT DOCUMENTS

EP 1684673 7/2010

OTHER PUBLICATIONS

Pioneer Surcical, "PAC Plate," 2010, 2 pages.
X-Spine Systems, Inc., "Spider Cervical Plating System," 2010, 2 pages.
Roham Moftakhar, M.D., et al., "Anterior cervical plates: a historical perspective," Jan. 2004, 5 pages.

*Primary Examiner* — Si Ming Ku

(74) *Attorney, Agent, or Firm* — Trop, Pruner and Hu, P.C.

(57) ABSTRACT

An embodiment of the invention provides for a system, such as a cervical plate fusion system, that has mechanisms for preventing bone anchors (e.g., screws, pins, and the like) from backing out of the plate. The system prevents both counter-rotation of the screw and axial backing out of the screw. Other embodiments are described herein.

19 Claims, 16 Drawing Sheets

(56) References Cited

U.S. PATENT DOCUMENTS

| | | |
|---|---|---|
| 2005/0010227 A1 | 1/2005 | Paul |
| 2006/0161157 A1 | 7/2006 | Mosca |
| 2006/0195100 A1 | 8/2006 | Kirschman |
| 2008/0021470 A1 | 1/2008 | Ross |
| 2008/0021476 A1 | 1/2008 | Kirschman |
| 2009/0012571 A1 | 1/2009 | Perrow |
| 2009/0024170 A1 | 1/2009 | Kirschman |
| 2009/0275990 A1 | 11/2009 | Enayati |
| 2010/0262191 A1 | 10/2010 | Marik et al. |
| 2011/0319893 A1 | 12/2011 | Stanaford |

RESILIANT SPINAL PLATE SYSTEM

This application is a continuation of U.S. patent application Ser. No. 14/724,323, filed May 28, 2015, and entitled "Resiliant Spinal Plate System", which claims priority to U.S. Provisional Patent Application No. 62/003,984 filed on May 28, 2014 and entitled "Resiliant Spinal Plate System". The content of each of the above applications is hereby incorporated by reference.

BACKGROUND

Spinal fixation devices can be used to provide, for example, immobilization and stabilization of spinal segments in patients (e.g., humans, dogs, cats, and other animals). Fixation devices may be used to help fuse bone segments (e.g., vertebrae) in the treatment of instabilities or deformities of, for example, the cervical, thoracic, lumbar, and/or sacral spine. Such instabilities or deformities may include, for example, degenerative disc disease (DDD); spondylolisthesis; trauma (i.e., fracture or dislocation); spinal stenosis; curvatures (i.e., scoliosis, kyphosis, and/or lordosis); tumor; pseudoarthrosis; and failed previous fusions.

However, there are risks associated with such fixation devices. Such risks include, for example, device component fracture, loss of fixation when the device/tissue bond is weakened or lost, non-union, fracture of the vertebra, neurological injury, and vascular or visceral injury. For example, internal fixation appliances are load sharing devices used to obtain bone alignment until normal healing occurs. Thus, implants are subjected to loads such as repetitive loads that occur when fixation systems are subjected to loading associated with, for example, normal patient movements (e.g., walking and bending), delayed union, or non-union situations. These loads can cause screws, which couple a fixation plate to bone, to loosen. The screws may loosen by, for example, backing out. This "backing out" may occur due to unwanted screw rotation (e.g., when the screw rotates and "unscrews" from the bone) and/or unwanted screw axial movement that is directed away from the bone. The axial movement may or may not be caused by the unwanted screw rotation. When a screw or screws back out and away from the plate and bone, the plate may become unstable and lead to complications for the patient. The degree or success of union, loads produced by weight bearing, and activity levels will, among other conditions, dictate the longevity of the implant. Robust fixation systems are needed to lessen risks associated with fixation and to promote better outcomes for patients.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" and the like describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical contact with each other and "coupled" may mean that two or more elements co-operate or interact with each other, but they may or may not be in direct physical contact.

An embodiment of the invention provides for a system, such as a cervical plate fusion system, that has mechanisms for preventing bone anchors (e.g., screws, pins, and the like) from backing out of the plate. The system prevents both counter-rotation of the screw and axial backing out of the screw. Other embodiments are described herein.

FIGS. 1-16 include plate 100. Plate 100 may be used for fusion of cervical vertebrae but may also be used for fusion of other vertebrae (e.g., thoracic, lumbar) or for fixation of other tissues (e.g., adjacent bone sections of a femur or other bone or tissue) and the like.

Figure 1:
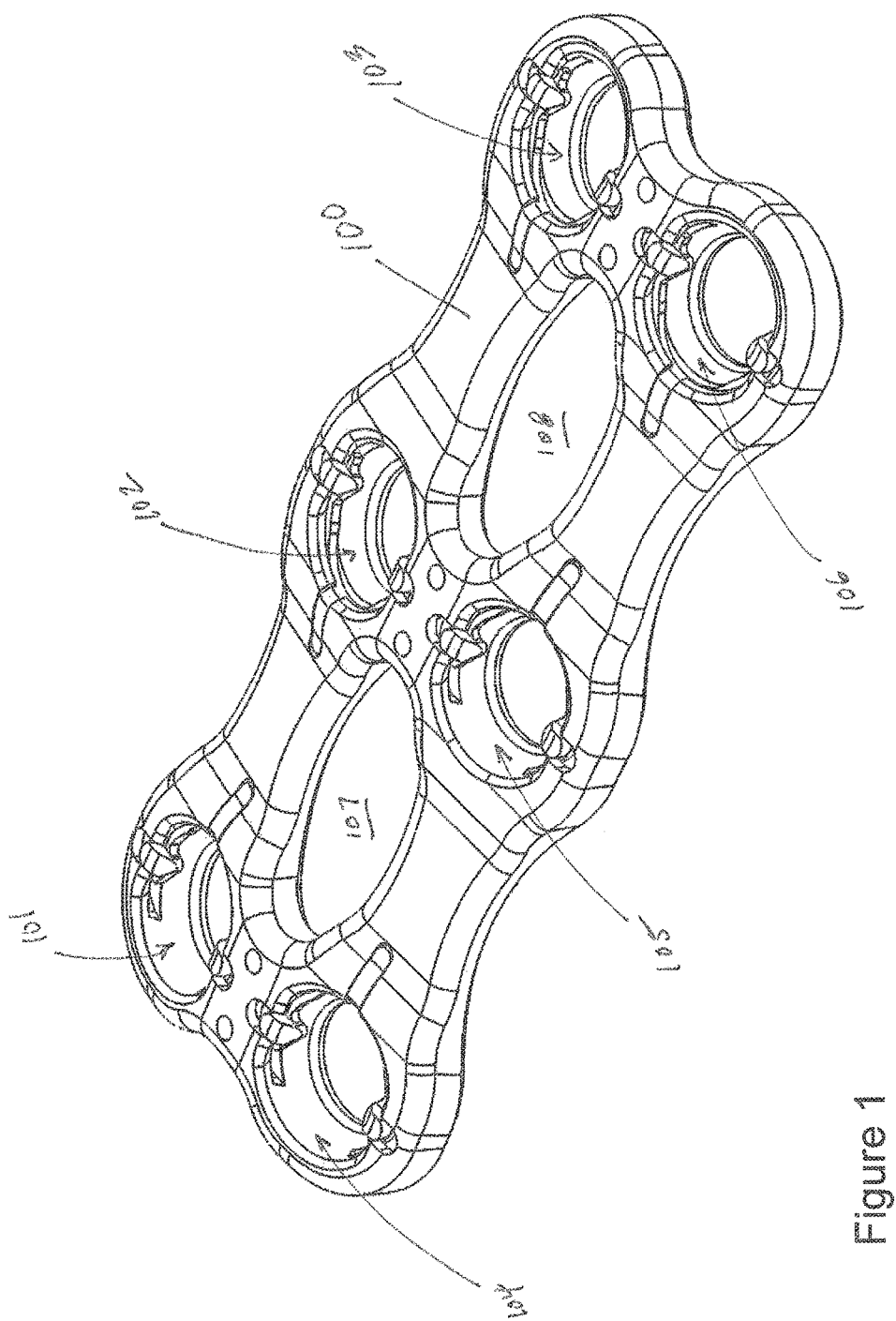
FIGS. 1-16 include different perspectives of a plate and resilient retaining member in embodiments of the invention.
Figure 2:
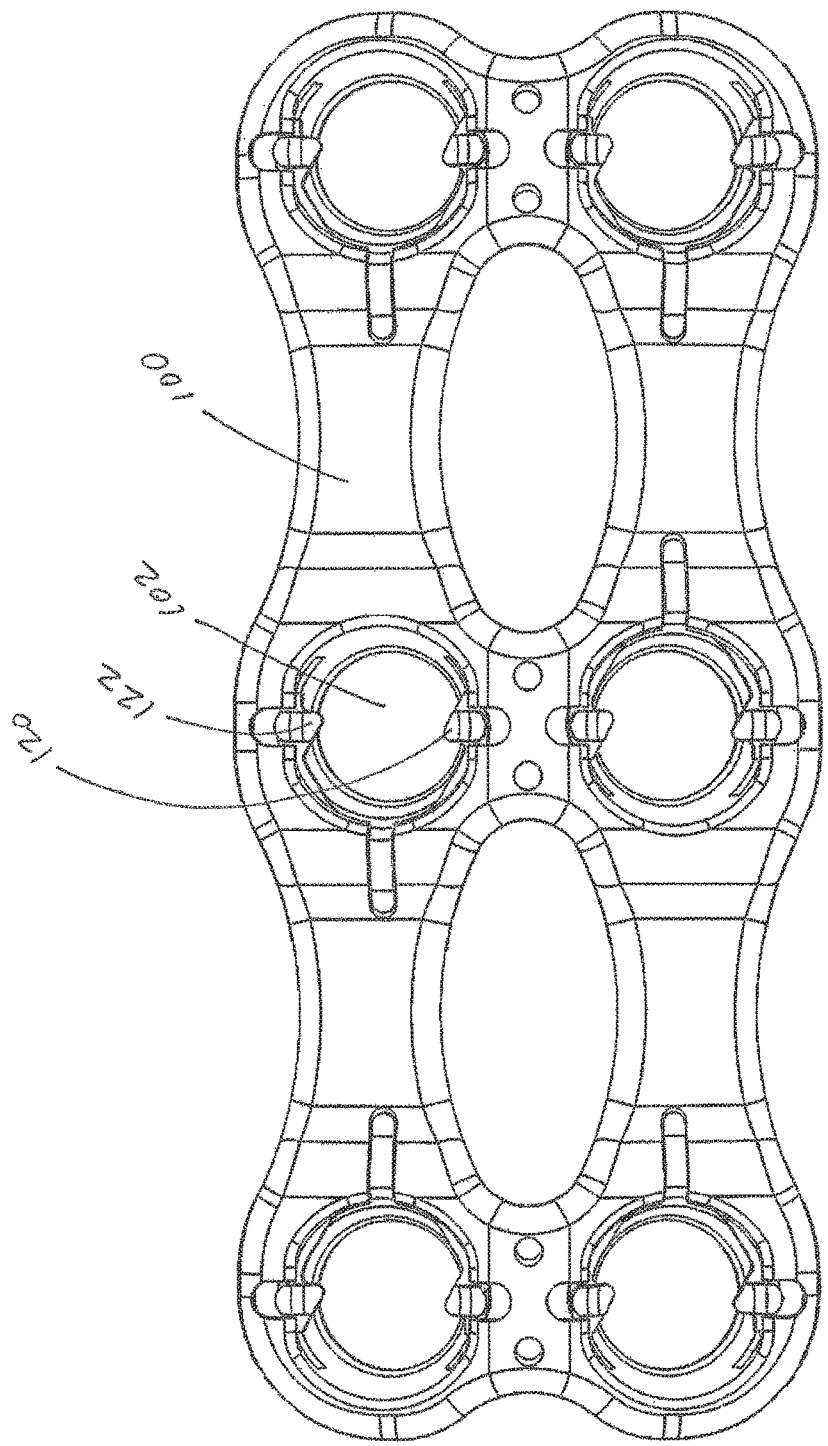
Figure 3:
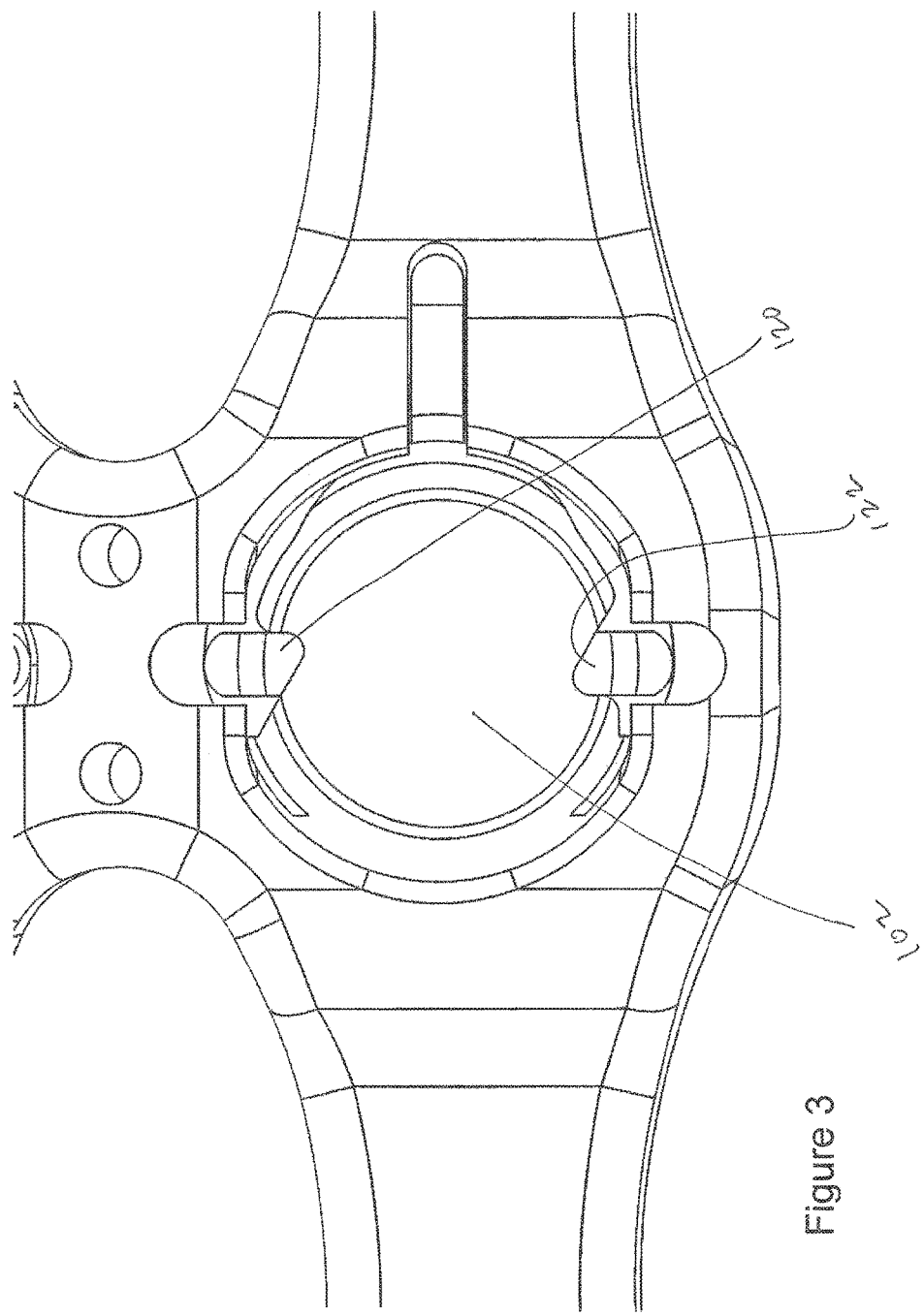

In FIG. 1, plate 100 includes apertures 101, 102, 103, 104, 105, 106. These apertures or holes may have continuous perimeters but may also include discontinuous perimeters that do not form a complete circle, oval, rectangle and the like. The apertures (e.g., holes) need not be circular, symmetrical, or have any one particular perimeter, even though apertures 101, 102, 103, 104, 105, 106 each include a generally continuous circular perimeter. The three pairs of holes (101 and 104, 102 and 105, 103 and 106) of plate 100 are for a two level fusion system where two vertebral discs are to be fused. For example, only holes 101, 102, 104, 105 would be needed for a one level fusion. A fourth pair of holes may be needed for a three level fusion.

Figure 6:
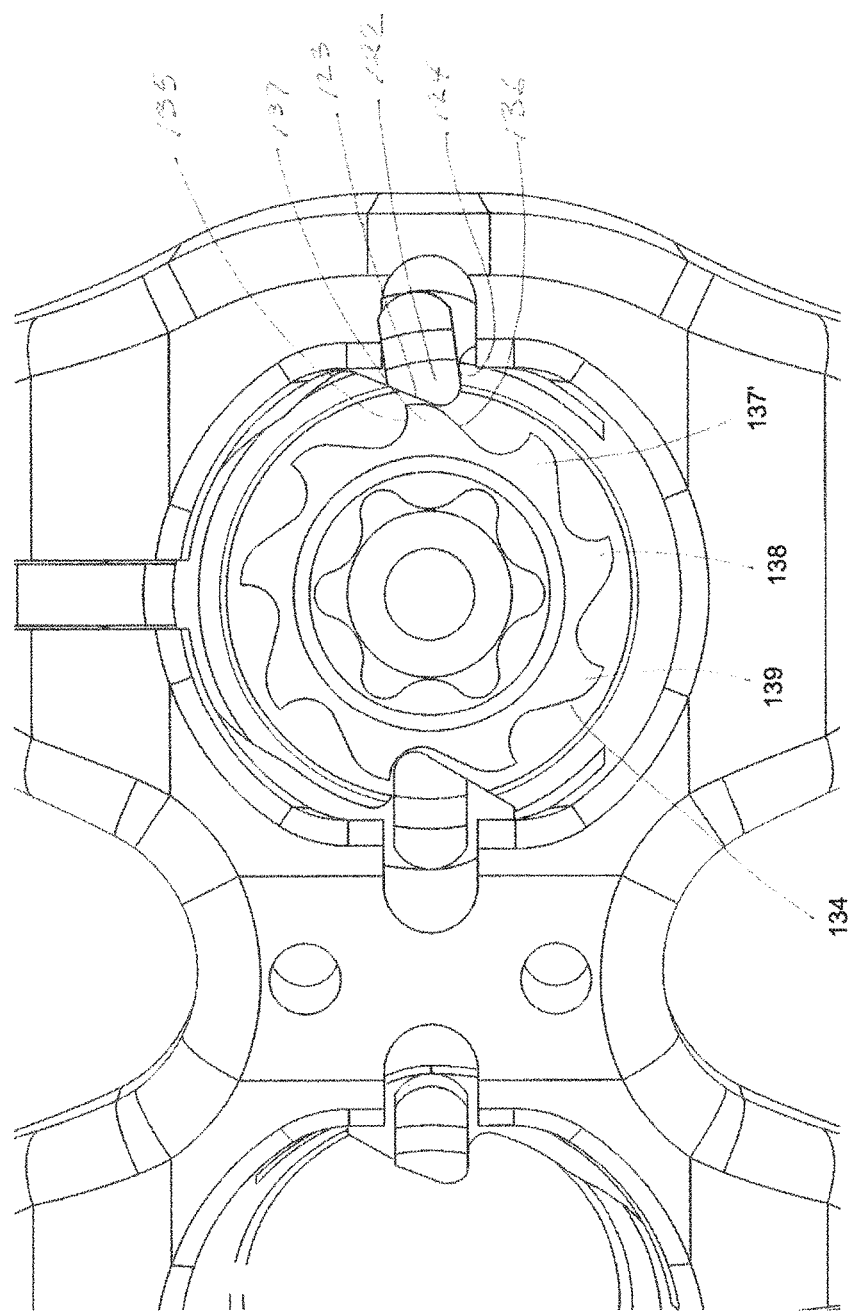
Figure 7:
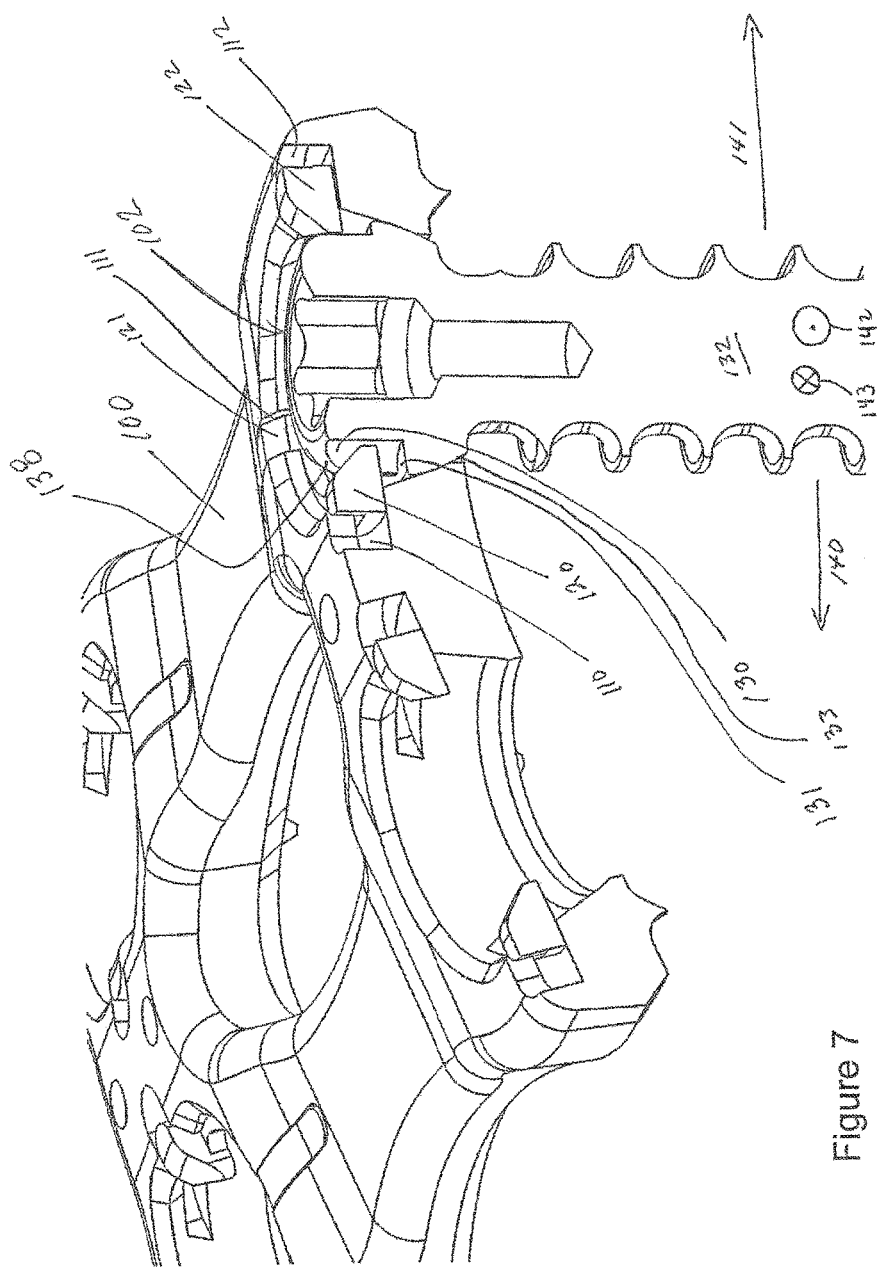
Figure 12:
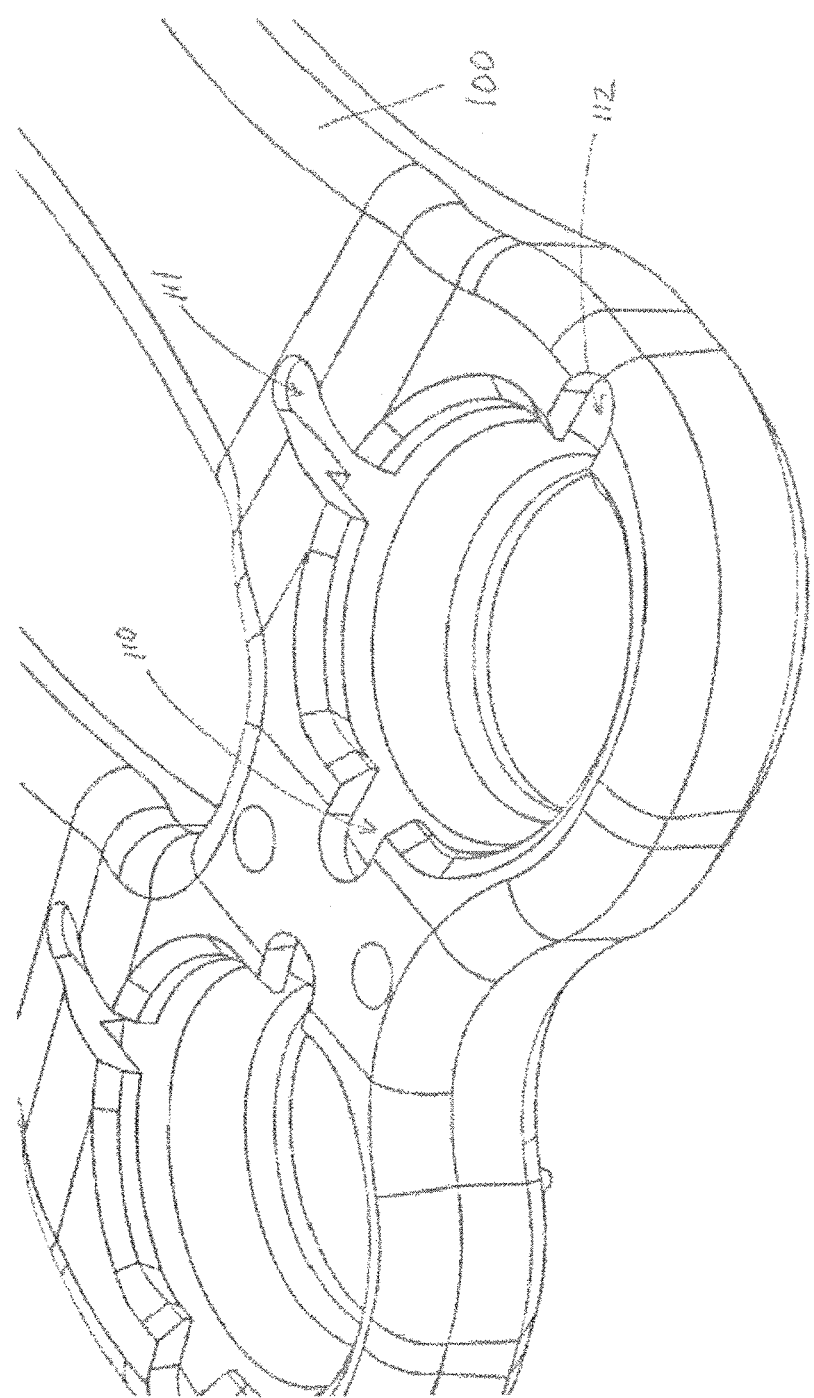
Figure 13:
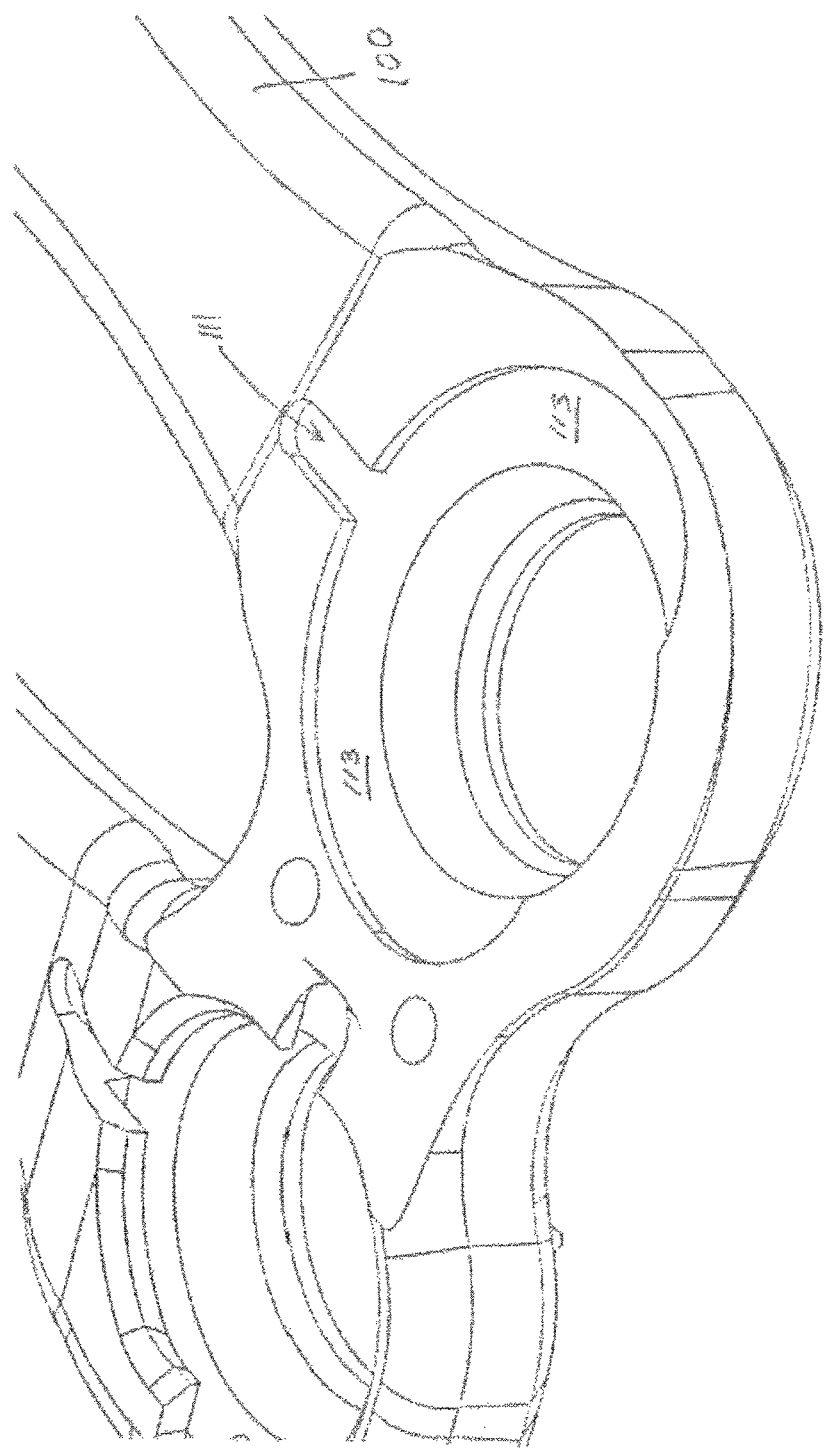
Figure 14:
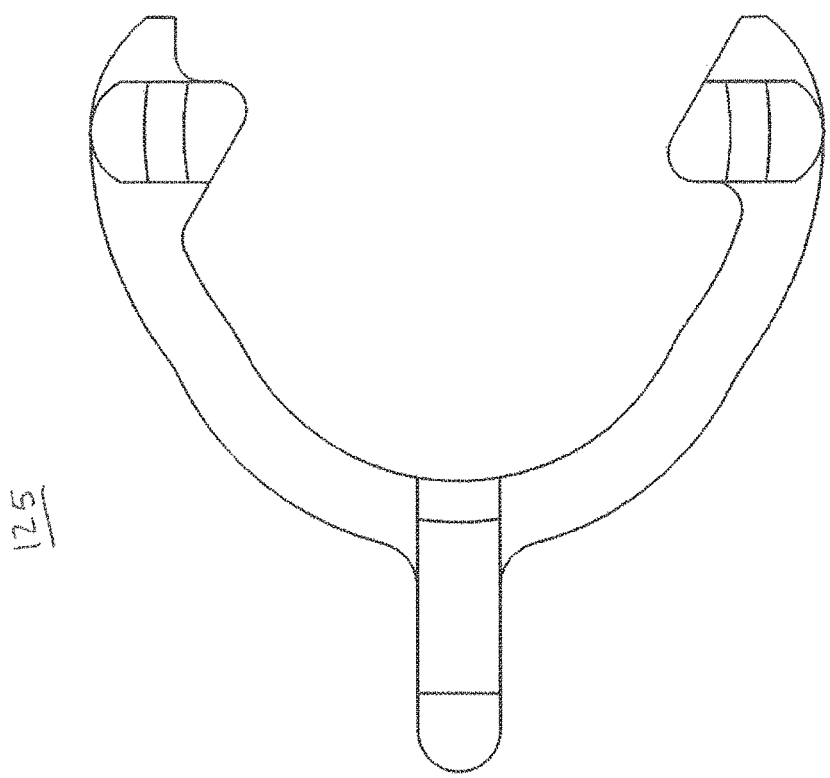
Figure 15:
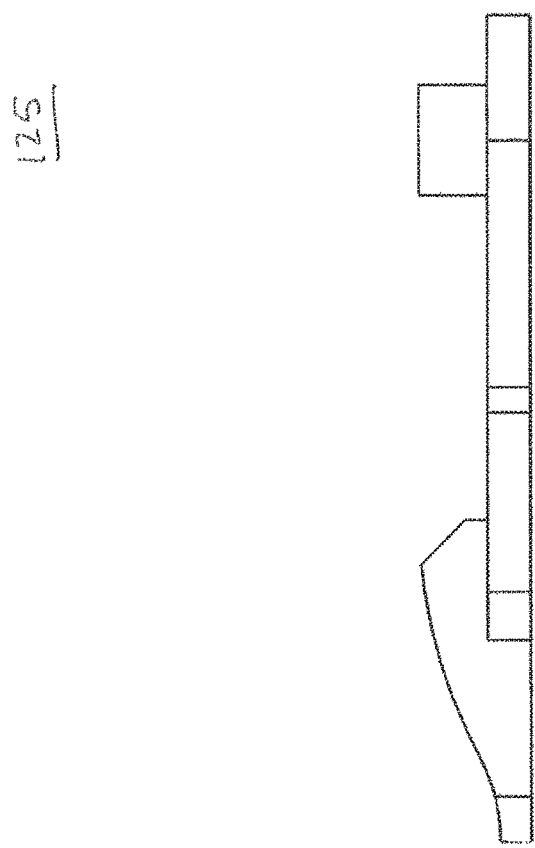
Figure 16:
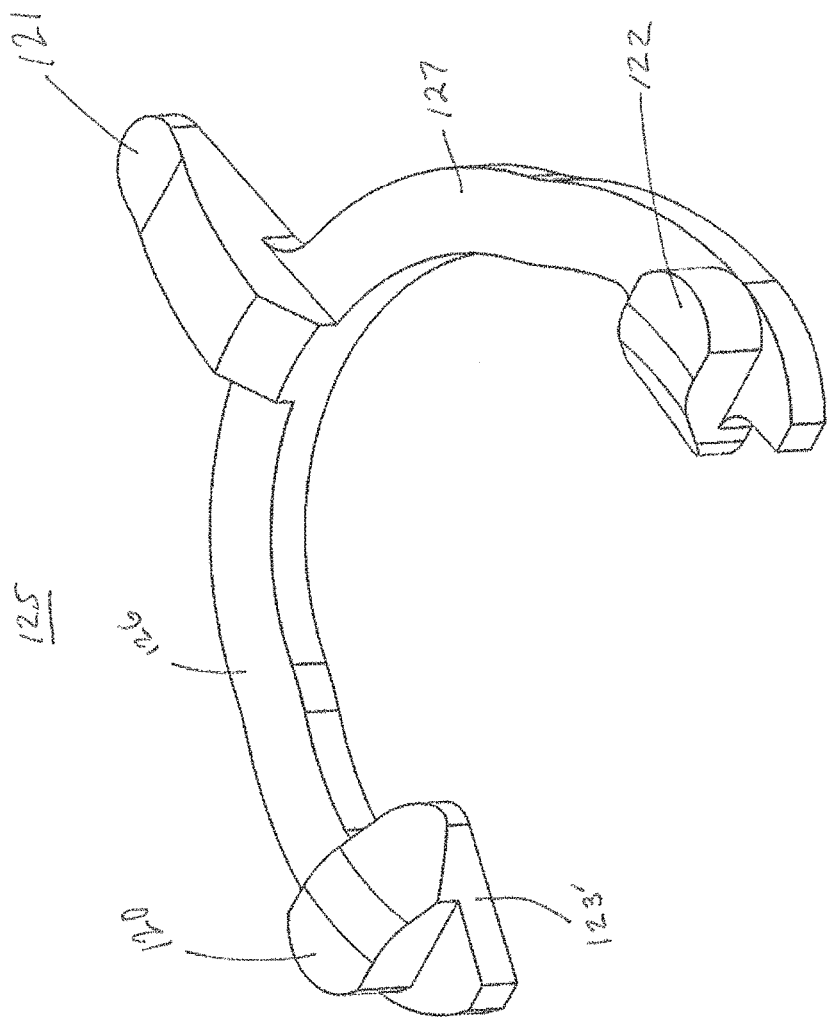

In FIG. 12, plate 100 includes cavities 110, 111, 112. These cavities are provided for each of apertures 101, 102, 103, 104, 105, 106. In FIG. 16, a single-piece monolithic resilient member 125 includes projections 120, 121, 122 that respectively fit within cavities 110, 111, 112. During manufacturing member 125 may be formed in the "horseshoe" pattern shown in FIG. 16. The member may be formed as a single monolithic element with no weldings or fixtures used to assemble member 125. In FIGS. 6 and 7, screw 132 includes lip 131, which is coupled to an angled or beveled shoulder 133, and a toothed wheel 134 having teeth such as tooth 138 and tooth 139.

A method addresses various embodiments of the invention. For example, a user inserts screw 132 into hole 102 of plate 100. Cavities 110, 111, 112 respectively include portions 120, 121, 122 of resilient member 125. Fins or projections 120, 122 respectively project into hole 102. Thus, at least a portion of fins 120, 122 project into hole 102.

In an embodiment, resilient member 125 is seperably coupled to plate 100. For example, during assembly (e.g., at a manufacturing plant, in an operating room, in a medical office, etc.) member 125 may be compressed and then inserted into cavity 113, which includes channels 110, 111, 112. In an embodiment, member 125 is retained within cavity 113 (shown with portions of plate 100 cut away in FIG. 13 to better show cavity 113) based on a resistance fit where member 125 does not require use of a weld, screw, clamp, or the like to hold member 125 within cavity 113. Consequently, member 125 has advantages related to ease of manufacturing and also related to ease of assembly into plate 100. Placing member 125 within (partially or fully) cavity 113 helps reduce the overall profile of the plate system, thus providing a less intrusive system for the patient.

As seen in FIG. 6, fin 122 has an angled leading edge 123 and a trailing edge 124, leading edge 123 being non-orthogonally connected to arm 127. As seen in FIG. 16, fin 120 has an angled leading edge 123' non-orthogonally connected to arm 126. Regarding the screw that interfaces member 125, FIG. 6 shows how tooth 137 has angled leading edge 136 and curved trailing edge 135. Fin 122 is sized to be received between teeth 137, 137' of toothed wheel 134.

FIG. 7 depicts an embodiment of the invention with a screw inserted into a hole.

Returning to the method, shoulder 133 of screw 132 deflects member 125. Specifically, when screw 132 is in a partially implanted position and is being inserted into hole 102 beveled shoulder 133 is actively deflecting fins 120 and/or 122 medially or laterally respectively.

As the method continues the user advances screw 132 into a fully implanted position such that screw 132 is prevented from backing out of hole 102 by fin 120 and/or 122. At this point fin 120 and/or 122 has snapped back towards the center of aperture 102 after having been deflected (medially (if fin 120) or laterally (if fin 122)) respectively into channels 110, 112 to now intercept lip 131 if and when screw 132 "backs out" or travels (or attempts to "back out" or travel) axially away from patient bone in which it is implanted. Also, while toothed wheel 134 is allowed to rotate in one direction (e.g., clockwise to tighten screw 134 into bone) toothed wheel 134 is prevented from counter-rotating (e.g., counter clockwise to loosen and "back out" from bone) because trailing edge 124 of fin 122 is lodged against trailing edge 135 of tooth 137. In FIG. 7, members 120 and 122 have both "snapped back" towards the middle of hole 102.

In FIG. 1, plate 100 includes viewing apertures 107, 108 which allow patient tissue to be viewed by a user upon implantation of the system into a patient. Bone tissue may be inserted through apertures 107, 108 to facilitate fusion. As seen in FIG. 1, no resilient member (e.g., member 125) projects into either of apertures 107, 108. Also, cavity 113 does not connect to either of apertures 107, 108.

In an embodiment, member 125 includes nitonol. However, in other embodiments member 125 includes other materials such as stainless steel and the like. In an embodiment, member 125 includes a "horseshoe" shaped profile but may include other shaped profiles (e.g., a bracket, such as a structure similar to an American football field goal having one or two support members that couple to a "U" or bracket shaped portion having two arms extending away from the one or to two support members) in other embodiments.

Figure 4:
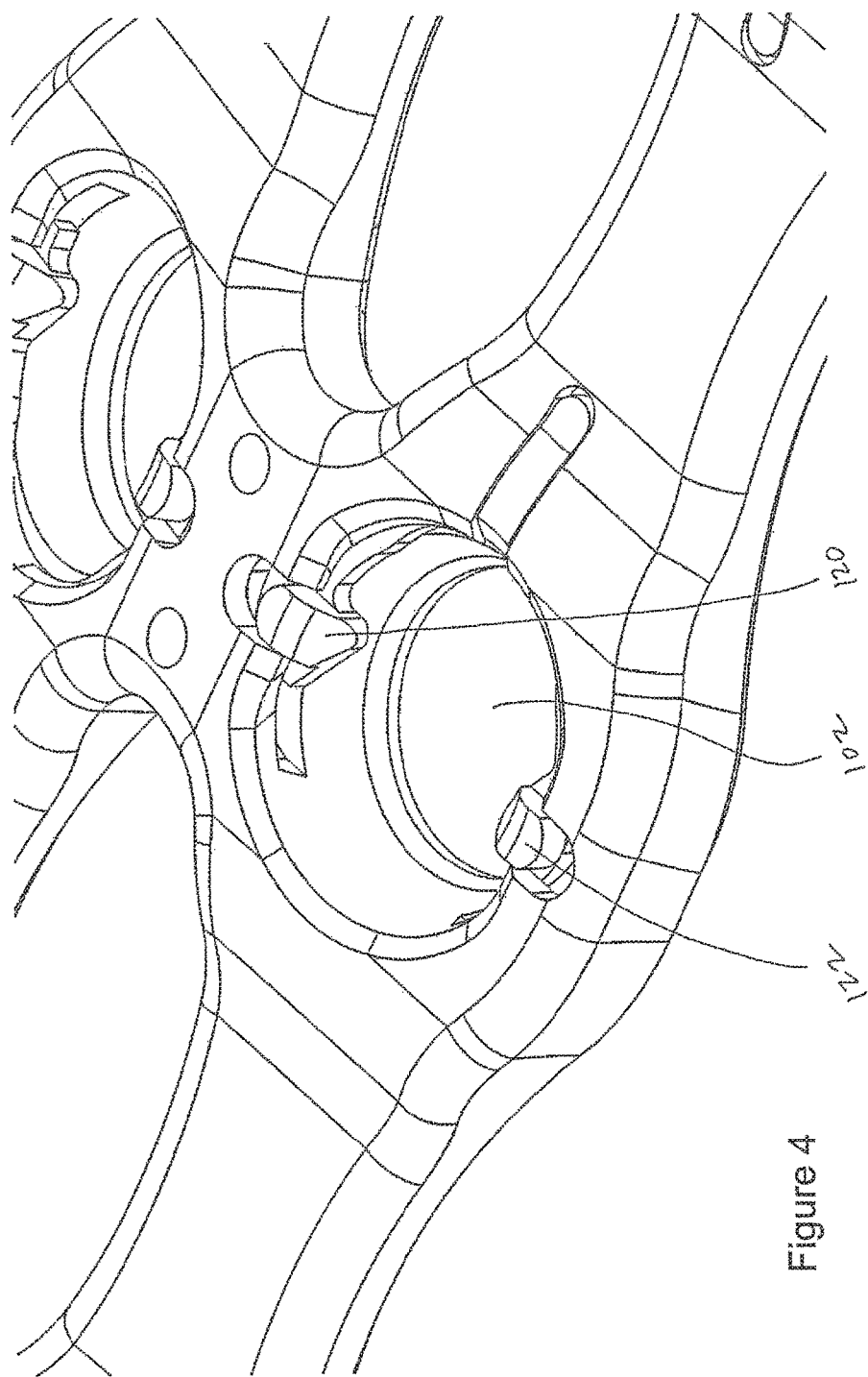
Figure 5:
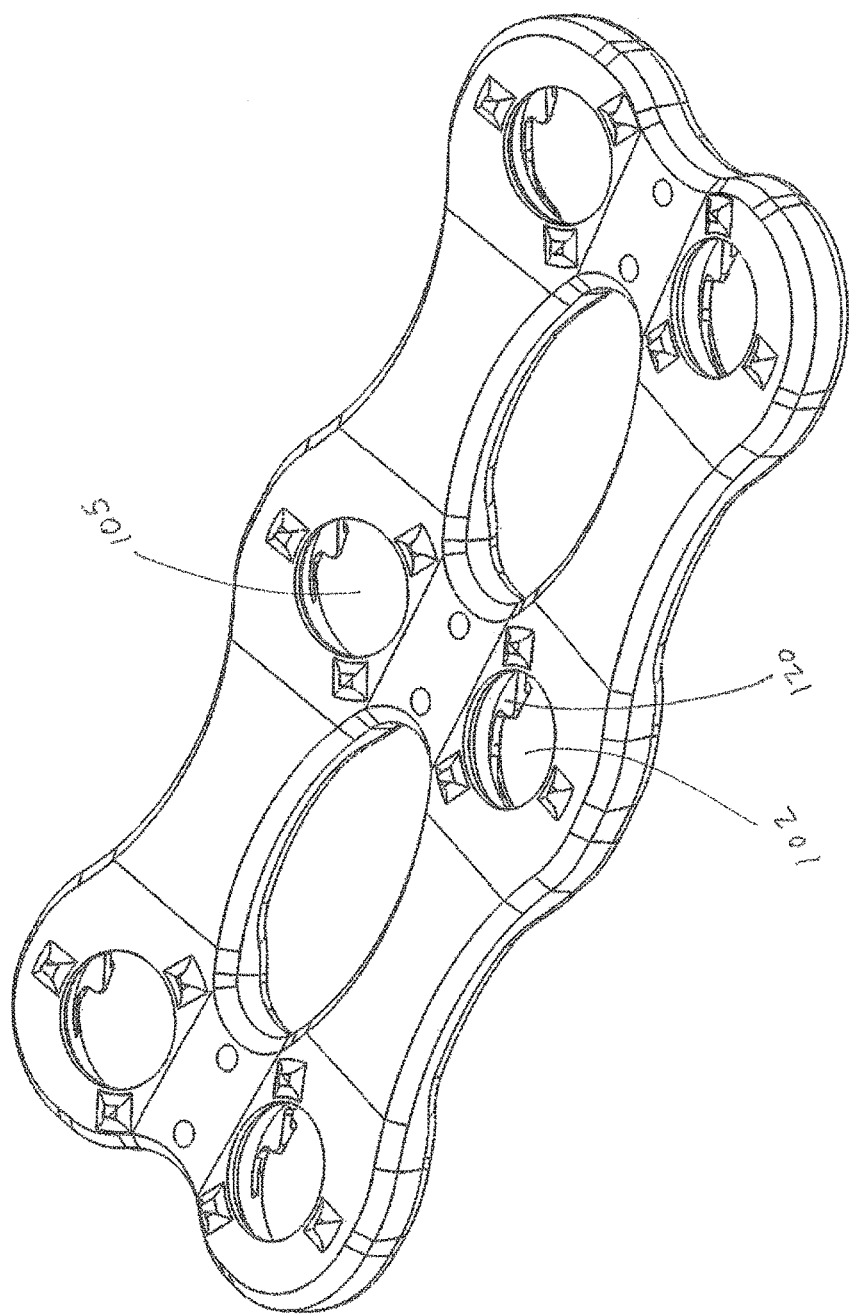

In an embodiment, screw 132 includes tooth 138, which has a height sized so when the screw is fully implanted (e.g., with shoulder 133 directly against bone) fin 120 will always be in contact with a portion of tooth 138. In other words, in an embodiment fin 109 projects medially out from "T" channel 421 (FIG. 4). If the tooth height is too small, fin 120 could spring or project over tooth 138 and possibly loose contact with tooth 138. In such a case screw 132 may begin working loose when not in constant contact with a tooth included on the toothed wheel because there would be no immediate barrier to axial "back out" movement and/or loosening counter-rotation. However, such a scenario may be mitigated or eliminated by properly sizing the tooth height so when the screw is fully implanted fin 120 will always be in contact with a portion of tooth 138.

In an embodiment, a horizontal axis 199 intercepts first and second fins of 120', 120" two resilient members (e.g., medial fins of resilient members in a pair of apertures such as apertures 101, 104), does not intercept a lateral wall portion 198 of hole 101, does intercept a medial wall portion 197 of hole 101, and does not intercept fins 122', 122". Thus curvature of the plate provides for proper lordosis and can be seen in FIGS. 10-11. Also, the horizontal axis intercepts the first and second medial fins of a single level (e.g., medial fins of resilient members 125 in apertures 101, 104). The design of the system allows for scaling between various embodiments that correspond to varying fusion levels whereby different embodiments suited for different levels of fusion use different numbers of identical resilient members, regardless of where the resilient members are located in the plates.

In various embodiments screw 132 includes an overall height (proximal end or head to distal end or tow) of generally 1.2, 1.3, 1.4, 1.5, 1.6, 1.7, or 1.8 mm.

In various embodiments, a plate may forego use of a cavity (that corresponds to a resilient member) and may instead couple the resilient member to an outer surface of the plate. The resilient member may also be integral or monolithic with the plate. Also, fins may include various geometries and may include, for example, orthogonal dimensions such that the fin has straight edges that fit at right angles to an arm of resilient member. The fin may be rectangular, square, and the like. The same may be the case for teeth on the screw such that the teeth may have straight edges that fit at right angles to the toothed wheel.

Also, embodiments do not necessarily require that the screw include a "highly" toothed wheel but may also include a screw with a few (e.g., one or two) simple projections that serve as teeth to accomplish the goal of preventing unwanted rotation. Also, while "rotation" and "counter rotation" have been used herein those terms should not be assumed to be associated with, for example, any particular direction such as "clockwise" for "rotation" or "counter clockwise" for "counter rotation." Also, screws may include lips that are not necessarily limited to flanges and the like. Lips may include floors or basic impediments to, for example, vertical or axial movement away from bone.

Embodiments described herein have many advantages.

First, in an embodiment projection 121 fits within aperture 111 thereby preventing rotation of member 125 within channel 113. Thus, member 125 is securely fitted within slot 113 even if only by resistance fit (although portions of member 125 may be coupled to plate 100 using welds, adhesives, and the like in other embodiments).

Second, in an embodiment member 125 provides two fins 120, 122 to engage surface 131 of screw 132. This is in contrast to conventional systems that may provide only a single fin or surface for engaging a screw and preventing back out by the screw. This can be a critical issue considering screw 132 is not always implanted straight into a bone but may instead be offset towards direction 140 (FIG. 7), which would cause surface 131 to rotate towards fin 120 but away from fin 122. Furthermore, screw 132 may be offset towards direction 141, which would cause surface 131 to rotate towards fin 122 but away from fin 120. This prevents the screw head from working past all the fins of a system because even if one of the fins (120, 122) is not in contact or in line to stop screw 132 from backing out, the other of the fins (120, 122) will be in contact or in line to stop screw 132 from backing out. If a conventional system were to only have a single projection, such as something roughly analogous to fin 120, offset of screw 132 along direction 141 may cause surface 131 to be able to back out past the portion analogous to fin 120 (or even if screw 132 does not blackout past the portion analogous to fin 120, there may be a lack of stability if nothing analogous to fin 122 is present).

Third, in an embodiment fins 120, 122 are 180 degrees from one another. In such a scenario screw 132 may be offset towards direction 142 (out of the page for FIG. 7), but doing so would not cause surface 131 to rotate away from either of fins 120, 122 (but instead merely pivot about fins 120, 122). In such a scenario screw 132 may be offset towards direction 143 (into the page for FIG. 7), but doing so would not cause surface 131 to rotate away from either of fins 120, 122 (but instead merely pivot about fins 120, 122).

Figure 8:
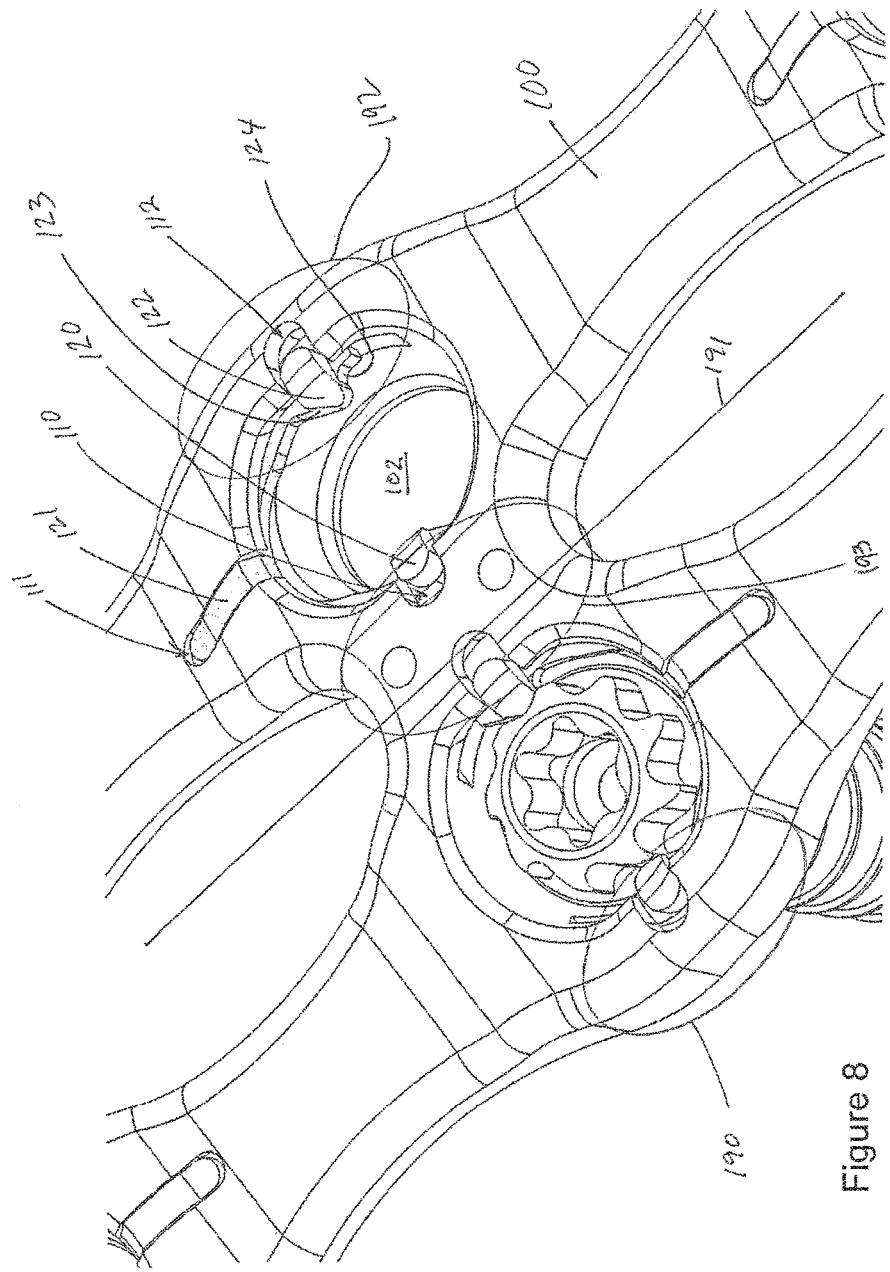
Figure 9:
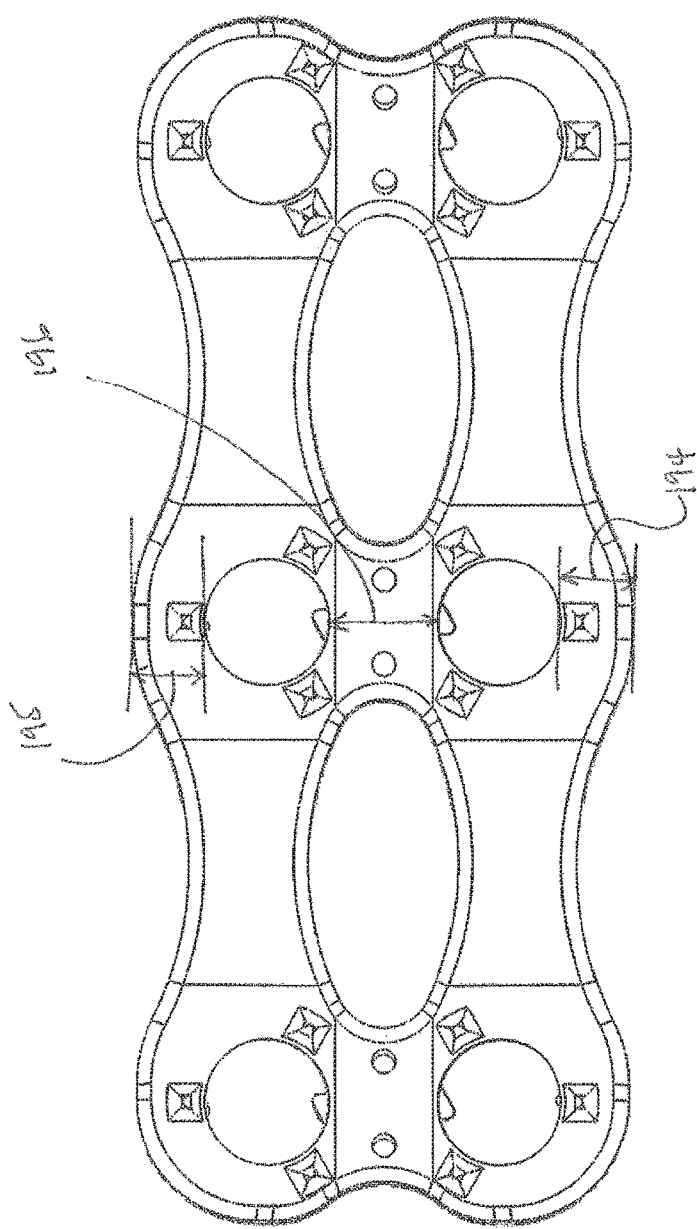
Figure 10:
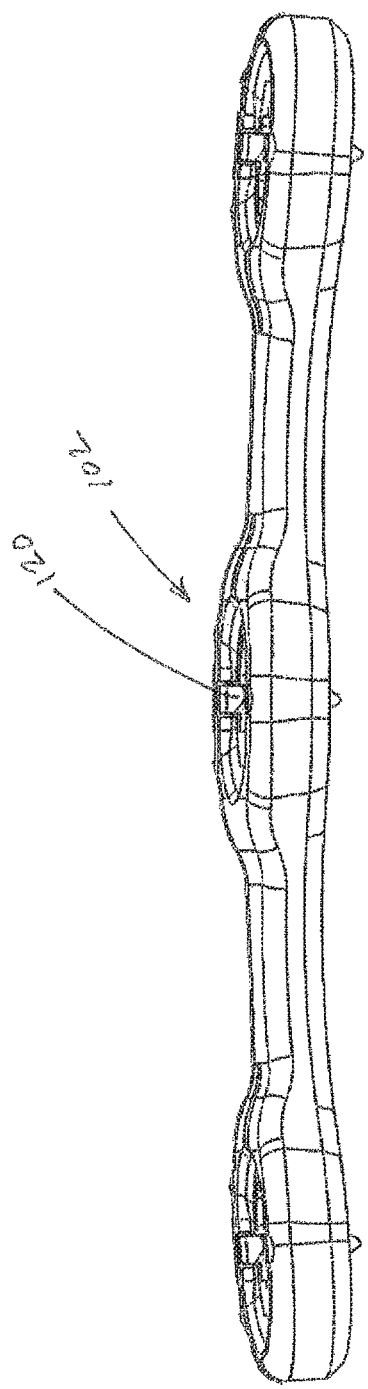
Figure 11:
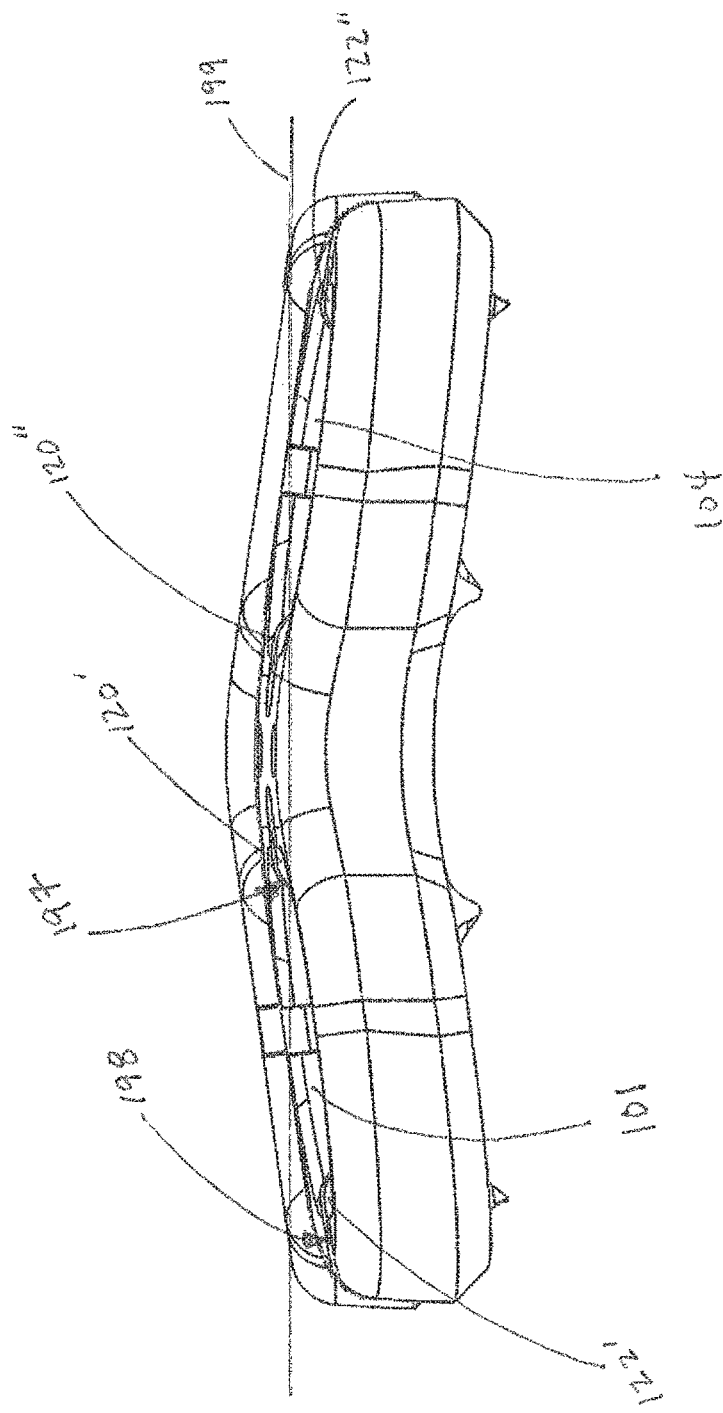

Fourth, anti-rotation member 121 may be formed parallel to a long main axis 191 that bisects graft windows 107, 108 (see FIGS. 1 and 8). By forming member 121 in this location an embodiment may allow for a thinner sidewall portion 190 (as measured orthogonal to the long axis 191). In an embodiment the sum of the widths (as measured orthogonal to the long axis 191) of portions 190, 192 is less than the width of middle portion 193. This creates a smaller profile which can be desirable for the patient. For example, in FIG. 9 the sum of distances 194, 195 may be less than distance 196.

While four specific advantages are addressed immediately above, not every embodiment requires each of those four advantages. For example, member 121 may be unnecessary in some embodiments if slot 113 is also in a horseshoe pattern and does not allow for rotation of the resilient member. Further, some embodiments do not necessarily place fins 180 degrees from each other but may instead place them 170, 160, 145, 130, 120, 110, 90, 70, 60, 40 degrees from one another. An embodiment includes an orthopedic fusion system comprising: a plate that includes a first aperture; a single-piece monolithic resilient member included in a first cavity that directly contacts the first aperture, the resilient member including a first arm connected to a first end having a first fin and a second arm connected to a second end having a second fin; a screw including a lip, which is coupled to a beveled shoulder, and a toothed wheel having first and second teeth; wherein (a) the resilient member is seperably coupled to the plate and within the first cavity; (b) the first cavity includes first and second channels that respectively include first and second portions of the first and second ends; (c) the first and second fins respectively project into the first aperture; (d) the first fin has a first angled leading edge and a first curved trailing edge, the first angled leading edge of the first fin being non-orthogonally connected to the first arm; (e) the first tooth has a first angled leading edge and a first curved trailing edge, the first angled leading edge of the first tooth being non-orthogonal to a tangent intersecting the toothed wheel at a point where the first angled leading edge of the first tooth intersects the toothed wheel; and (f) the first fin is sized to be received between the first and second teeth of the toothed wheel; wherein the system is configured such that (g) in a partially implanted position the screw is inserted into the first aperture and the beveled shoulder is actively deflecting the first fin medially and the second fin laterally; and (h) in a fully implanted position (1) the screw is inserted into the first aperture such that the screw is prevented from backing out of the first hole by the first and second fins that have snapped back into the first aperture to intercept the lip when the screws travels axially away from patient bone in which it is implanted and (2) the toothed wheel is allowed to rotate but is prevented from counter-rotating because the first curved trailing edge of the first fin is lodged against the first trailing edge of the first tooth.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An orthopedic fusion system comprising:
   a plate that includes a first aperture;
   a single-piece monolithic resilient member; and
   a screw including a lip;
   wherein:
   the plate includes a first cavity, the first cavity directly interfacing the first aperture;
   at least a portion of the resilient member is included in the first cavity;
   the resilient member includes an arcuate portion, a first resilient member projection, and a second resilient member projection;
   the arcuate portion couples the first resilient member projection to the second resilient member projection;
   the first resilient member projection projects into the first aperture and towards a center of the first aperture;
   the second resilient member projection projects into the first aperture and towards the center of the first aperture;
   the screw includes a shoulder, the shoulder being coupled to the lip;
   the screw includes a first screw projection and a second screw projection;
   the lip is between the first screw projection and the shoulder;
   the lip is between the second screw projection and the shoulder;
   the system is configured such that in a partially implanted position the screw is included in the first aperture and the shoulder actively deflects the first resilient member projection medially;
   the system is configured such that in the partially implanted position the screw is included in the first aperture and the shoulder actively deflects the second resilient member projection laterally;
   the system is configured such that in a fully implanted position the screw is included in the first aperture such that the screw is prevented from backing out of the first aperture by the first resilient member projection that has snapped back towards the center of the first aperture to intercept the lip;
   the system is configured such that in the fully implanted position the screw is included in the first aperture such that the screw is prevented from backing out of the first aperture by the second resilient member projection that has snapped back towards the center of the first aperture to intercept the lip; and
   the system is configured such that in the fully implanted position the screw is allowed to rotate but is prevented from counter-rotating because the first screw projection is lodged against the first resilient member projection.

2. The system of claim 1 wherein the resilient member is seperably coupled to the plate.

3. The system of claim 2 wherein the resilient member is seperably coupled to the plate via a resistance fit between the resilient member and the first cavity.

4. The system of claim 1 wherein in an additional orientation:
a vertical axis of the plate is orthogonal to a horizontal axis of the plate; and
the horizontal axis intersects the first screw projection; and
the horizontal axis intersects the second screw projection.

5. The system of claim 1 wherein the first and second resilient member projections are substantially 180 degrees from one another along the arcuate portion.

6. The system of claim 1 wherein the first and second resilient member projections directly oppose one another.

7. The system of claim 1 wherein:
the first resilient member projection substantially points laterally and deflects medially in the partially implanted position; and
the second resilient member projection substantially points medially and deflects laterally in the partially implanted position.

8. The system of claim 1, wherein:
the plate includes a second aperture, first and second lateral portions, and a middle portion;
the second aperture is adjacent the first aperture;
the first lateral portion is lateral to the first aperture;
the second lateral portion is lateral to the second aperture;
the middle portion is between the first and second apertures;
a vertical axis of the plate is orthogonal to a horizontal axis of the plate;
the horizontal axis intersects the first lateral portion along a first distance, the first distance extending laterally from the first aperture to a first lateral edge of the plate;
the horizontal axis intersects the second lateral portion along a second distance, the second distance extending laterally from the second aperture to a second lateral edge of the plate;
the horizontal axis intersects the middle portion along a third distance, the third distance extending from a first medial portion of the first aperture to a second medial portion of the second aperture; and
a sum of the first and second distances is no greater than the third distance.

9. The system of claim 1 comprising:
a second aperture adjacent the first aperture;
a second cavity included in the plate, the second cavity directly interfacing the second aperture;
an additional single-piece monolithic resilient member that is at least partially included in the second cavity;
wherein:
the additional resilient member includes an additional arcuate portion, an additional first resilient member projection, and an additional second resilient member projection;
a horizontal axis, orthogonal to a vertical axis of the plate, intercepts the first resilient member projection and the additional first resilient member projection but does not intercept either of the second resilient member projection and the additional second resilient member projection.

10. The system of claim 1 wherein the screw includes third and fourth screw projections.

11. The system of claim 1 wherein the first resilient member projection has a first angled leading edge and a first trailing edge, the first angled leading edge of the first resilient member projection being non-orthogonally connected to the arcuate portion.

12. An orthopedic fusion system comprising:
a plate that includes a first aperture;
a single-piece monolithic resilient member; and
a screw including a lip;
wherein:
the plate includes a first cavity, the first cavity directly interfacing the first aperture;
at least a portion of the resilient member is included in the first cavity;
the resilient member includes an arcuate portion, a first resilient member projection, and a second resilient member projection;
the arcuate portion couples the first resilient member projection to the second resilient member projection;
the first resilient member projection projects into the first aperture and towards a center of the first aperture;
the second resilient member projection projects into the first aperture and towards the center of the first aperture;
the screw includes a shoulder, the shoulder being coupled to the lip;
the screw includes a first screw projection and a second screw projection;
the lip is between the first screw projection and the shoulder;
the lip is between the second screw projection and the shoulder;
the system is configured such that in a partially implanted position the screw is included in the first aperture and the shoulder actively deflects the first resilient member projection away from the center of the first aperture;
the system is configured such that in the partially implanted position the screw is included in the first aperture and the shoulder actively deflects the second resilient member projection away from the center of the first aperture;
the system is configured such that in a fully implanted position the screw is included in the first aperture such that the screw is prevented from backing out of the first aperture by the first resilient member projection that has snapped back towards the center of the first aperture to intercept the lip;
the system is configured such that in the fully implanted position the screw is included in the first aperture such that the screw is prevented from backing out of the first aperture by the second resilient member projection that has snapped back towards the center of the first aperture to intercept the lip; and
the system is configured such that in the fully implanted position the screw is allowed to rotate but is prevented from counter-rotating because the first screw projection is lodged against the first resilient member projection.

13. The system of claim 12 wherein:
the system is configured such that in the partially implanted position the screw is included in the first aperture and the shoulder actively deflects the first resilient member projection away from the center of the first aperture and along a first vector;
the system is configured such that in the partially implanted position the screw is included in the first aperture and the shoulder actively deflects the second resilient member projection away from the center of the first aperture and along a second vector;

the first vector is unequal to the second vector.

14. The system of claim 13 wherein the first vector is 180 degrees from the second vector.

15. The system of claim 13 wherein the screw includes third and fourth screw projections.

16. An orthopedic fusion system comprising:
a plate that includes a first aperture;
a single-piece monolithic resilient member; and
a screw including a lip;
wherein:
   at least a portion of the resilient member is included in the first aperture;
   the resilient member includes an arcuate portion, a first resilient member projection, and a second resilient member projection;
   the arcuate portion couples the first resilient member projection to the second resilient member projection;
   the first resilient member projection projects into the first aperture and towards a center of the first aperture;
   the second resilient member projection projects into the first aperture and towards the center of the first aperture;
   the screw includes a shoulder, the shoulder being coupled to the lip;
   the screw includes a first screw projection and a second screw projection;
   the lip is between the first screw projection and a portion of the shoulder;
   the lip is between the second screw projection and another portion of the shoulder;
   the system is configured such that in a first orientation the screw is at least partially included in the first aperture and the shoulder actively deflects the first resilient member projection away from the center of the first aperture;
   the system is configured such that in the first orientation the screw is at least partially included in the first aperture and the shoulder actively deflects the second resilient member projection away from the center of the first aperture;
   the system is configured such that in a second orientation the screw is at least partially included in the first aperture such that the screw is prevented from backing out of the first aperture by the first resilient member projection, the first resilient member projection having returned towards the center of the first aperture to intercept the lip in response to the shoulder no longer deflecting the first resilient member projection away from the center of the first aperture;
   the system is configured such that in the second orientation the screw is at least partially included in the first aperture such that the screw is prevented from backing out of the first aperture by the second resilient member projection, the second resilient member projection having returned towards the center of the first aperture to intercept the lip in response to the shoulder no longer deflecting the second resilient member projection away from the center of the first aperture; and
   the system is configured such that in the second orientation the screw is prevented from rotating in a first direction because the first screw projection is lodged against the first resilient member projection.

17. The system of claim 16 wherein:
the system is configured such that in the first orientation the screw is at least partially included in the first aperture and the shoulder actively deflects the first resilient member projection away from the center of the first aperture and along a first vector;
the system is configured such that in the first orientation the screw is at least partially included in the first aperture and the shoulder actively deflects the second resilient member projection away from the center of the first aperture and along a second vector;
the first vector is unequal to the second vector.

18. The system of claim 17 wherein the first vector is 180 degrees from the second vector.

19. The system of claim 16 wherein the screw includes third and fourth screw projections.

* * * * *